US00PP15115P2

(12) United States Plant Patent
Zary

(10) Patent No.: US PP15,115 P2
(45) Date of Patent: Aug. 31, 2004

(54) HYBRID TEA ROSE PLANT NAMED 'JACURNAM'

(50) Latin Name: *Rosa hybrida*
Varietal Denomination: JACurnam

(75) Inventor: Keith W. Zary, Somis, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 10/697,609

(22) Filed: Oct. 29, 2003

(51) Int. Cl.[7] ..... A01H 5/00
(52) U.S. Cl. ..... Plt./132
(58) Field of Search ..... Plt./132

*Primary Examiner*—Anne Marie Grunberg
*Assistant Examiner*—S B. McCormick-Ewoldt
(74) *Attorney, Agent, or Firm*—Klarquist Sparkman LLP

(57) ABSTRACT

Hybrid tea rose plant having exceptionally rich apricot blooms; compact well-branched hybrid tea plant habit; ability to grow vigorously on its own roots; resistance to powdery mildew and rust; large open flowers; and glossy, dark green foliage.

1 Drawing Sheet

Genus and species: *Rosa hybrida.*
Variety denomination: 'JACurnam'.

ORIGIN OF THE INVENTION

The present invention relates to a new and distinct variety of a hybrid tea rose plant named 'JACurnam' which was originated by me by crossing the variety 'JACient' (U.S. Plant Pat. No. 6,725), with an unnamed seedling (not patented).

BACKGROUND OF THE INVENTION

The primary objective of this breeding was to produce a new rose variety having the profuse flowering, excellent high disease resistant foliage, and vigorous growth of the female parent combined with the strong growth and disease resistance of the unnamed yellow hybrid tea male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Exceptionally rich apricot blooms.
2. Compact, well branched hybrid tea plant.
3. Ability to grow vigorously on its own roots.
4. Resistance to powdery mildew and rust.
5. Large open flower.
6. Glossy, dark green foliage.

Asexual reproduction of this new variety by cuttings, as performed at Wasco, Calif., shows that the foregoing and all other characteristics and distinctions come true to form and are established and transmitted through succeeding propagations.

COMPARISON WITH PARENTS

The subject variety differs in that the female parent has a pink flower coloring versus the rich apricot, clustering ability of 'JACurnam' (grandiflora versus hybrid tea). The male parent differs in flower color (yellow versus rich apricot) and flower size (9 cm versus 13 cm).

COMPARISON WITH SIMILAR VARIETY

The subject variety differs from Medallion in having a deeper apricot flower color, much shorter plant (150 cm versus 180 cm) than Medallion and a smaller flower size than Medallion (13 cm versus 15 cm).

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (2001), except where ordinary dictionary significance of color is indicated.

Parentage:
*Seed parent.*—'JACient' (U.S. Plant Pat. No. 6,725).
*Pollen parent.*—Unnamed seedling, (Not patented) (unnamed seeding×unnamed seedling).

Observations made from plants commencing at two years of age grown in a garden environment at Somis, Calif.

FLOWER

Blooming habit: Continuous.
Bud:
*Size.*—About 4 cm long and 3.5 cm in diameter when the petals start to unfurl.
*Form.*—The bud form is long, pointed ovoid.
*Color.*—When sepals first divide, bud color is Orange Red Group 34A. When half blown, the upper sides of the petals are Yellow Orange Group 23C on the bottom one-third of the petal and Yellow Orange Group 24B on the upper two-thirds. The petal edges fade to Orange Group 24D as the blooms open; and the lower sides of the petals begin in the bud as Orange Red Group 34A and change to Orange Red Group 32B.

*Sepals.*—Color: Upper surface: Green Group 138C, occasionally with a blush of Greyed Purple Group 184C. Lower surface: Green Group 146C. Length: 35–40 mm. Width: 7–8 mm. Shape: Subulate. Surface texture: Upper surface: Canescent. Lower surface: Pubescent. Margin: Cililate. There are three normally to heavily appendaged sepals. There are two unappendaged sepals with glandular edges.

*Receptacles.*—Color: Yellow Green Group 147B, often with a caste of Greyed Purple Group 183C. Shape: Funnel. Size: Medium, about 15 mm long×8 mm wide. Surface: Smooth.

*Peduncle.*—Length: Short, averaging about 5–6 mm. Surface: Glandular. Color: Yellow Green Group 147B. Strength: Strong.

Bloom:

*Size.*—Large. Average open diameter is about 12–13 cm.

*Borne.*—Singly.

*Stems.*—Strength: Strong. Average length is about 40–50 cm with a diameter of 4–6 mm.

*Form.*—When first open: High centered. Permanence: Flattens, outer petal edges curl slightly, with slight quilling.

*Petalage.*—Number of petals under normal conditions: 30.

*Color.*—The upper side of the petals are Yellow Orange Group 23C on the bottom one-third of the petal and Yellow Orange Group 24B on the upper two-thirds. The petal edges fade to Orange Group 24D as the blooms open. The reverse sides of the petals are Orange Red Group 34A in the tight bud and change to Orange Red Group 32B as the bud opens. The base of each petal has an intense 4 mm×4 mm Yellow Group 13A color spot. The major color on the upper side is Yellow Orange Group 24B.

*Variegations.*—None.

*Discoloration.*—The general tonality at the end of the first day: Little change. At the end of the third day: Fades on the outer one-fourth to one-third of the petal to Orange Group 24D.

*Fragrance.*—Moderate, spicy.

Petals:

*Texture.*—Thick, leathery.

*Shape.*—Round.

*Surface.*—Smooth.

*Margin.*—Entire. Apex Shape: Obtuse. Base Shape: Rounded.

*Form.*—Tips slightly recurved, edges slightly quilled.

*Arrangement.*—Regularly arranged, shingle-like.

*Petaloids.*—Number: 1 or 2 Color: Yellow-Orange Group 24B. Form: Gladiate. Size 20–30 mm. long× 8–12 mm. wide.

*Persistence.*—Petals drop off cleanly before drying.

*Lastingness.*—On the plant: Long (about 6 days). As a cut flower: Long (about 8–9 days).

Reproductive parts:

*Stamens.*—Number: 90–110. Length: 13–14 mm. Anthers: Length 2–3 mm. Color: Yellow-Orange Group 20B. Arrangement: Regular around styles. Filaments: Color: Yellow-Orange Group 21B. Length: 11–12 mm. Pollen: Color: Yellow-Orange Group 22A.

*Pistils.*—Number: 50–60. Length: 6–7 mm. Styles: Color: Red Group 46A. Length: 5–6 mm. Stigmas: Color: Yellow-White Group 158A. Length: 1 mm.

*Hips.*—None observed.

PLANT

*Form.*—Bush.

*Growth.*—Very vigorous, upright, branching.

*Age at maturity.*—Two years.

*Mature plant.*—Height: 150 cm. Width: 80 cm.

*Rootstock.*—Own roots.

Foliage: Number of leaflets on normal mid-stem leaves: 5 or 7.

*Size.*—Large. About 14 cm long×11 cm wide.

*Quantity.*—Abundant.

*Color.*—New foliage: Upper side: Greyed-Purple Group 183A. Lower side: Greyed-Purple Group 183D. Old foliage: Upper side: Green Group 136A. Lower side: Green Group N 138A.

Leaflets:

*Size.*—About 60 mm long×30 mm wide.

*Shape.*—Pointed oval.

*Base shape.*—Aequilateral.

*Apex shape.*—Acuminate.

*Texture.*—Leathery, glossy.

*Edge.*—Serrated.

*Serrations.*—Single.

*Petiole.*—Color: Yellow-Green Group 146D.

*Petiole rachis.*—Color: Yellow-Green Group 146B. Underside: Rough, with prickles.

*Auricle shape, if present.*—None.

*Stipules.*—Length: 13–14 mm, serrated. Shape: Adnate.

*Disease resistance.*—Resistant to mildew and rust and susceptible to blackspot under normal growing conditions.

*Pest resistance.*—None observed.

*Vein color.*—Green Group 139A.

*Venation pattern.*—Reticulate.

Wood:

*New wood.*—Color: Greyed-Purple Group 183B. Bark: Smooth.

*Old wood.*—Color: Green Group 139B. Bark: Smooth.

Prickles:

*Quantity.*—On main canes from base: Ordinary. On laterals from main canes: Ordinary.

*Form.*—Hooked downward.

*Length.*—5–6 mm.

*Color when young.*—Greyed-Purple Group 183A.

*Color when mature.*—Greyed-Orange Group 174A.

Small prickles:

*Quantity.*—On main stalks: None. On laterals: None.

*Color.*—None.

Winter hardiness: Hardy to Zone 5.

I claim:

1. A new and distinct variety of rose plant of the hybrid tea class, substantially as herein shown and described, characterized particularly by its exceptionally rich apricot blooms; compact well-branched hybrid tea plant habit; ability to grow vigorously on its own roots; resistance to powdery mildew and rust; large open flowers; and glossy, dark green foliage.

* * * * *

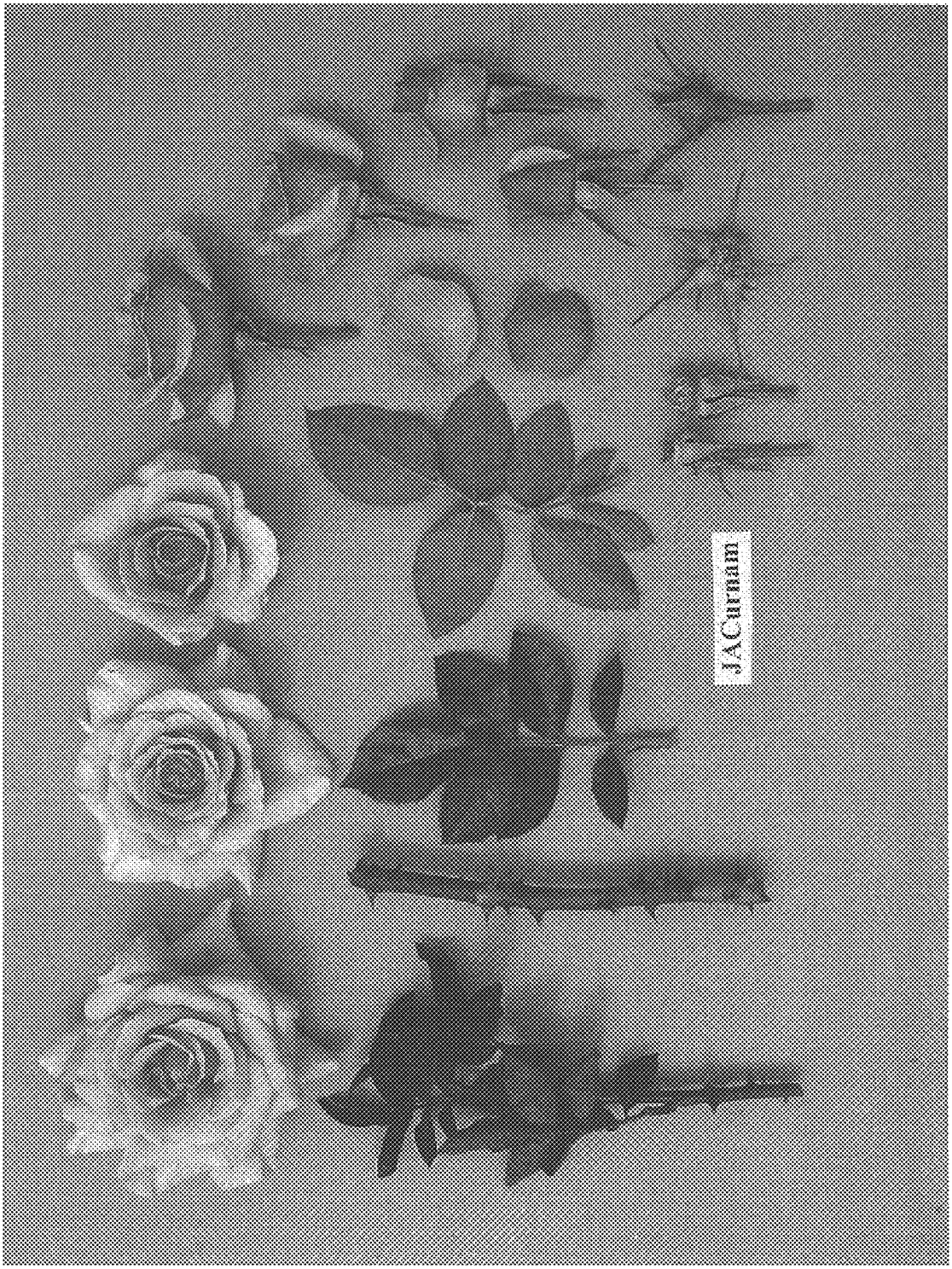
JACurnam